United States Patent [19]

De Heij et al.

[11] Patent Number: 5,313,002
[45] Date of Patent: May 17, 1994

[54] ETHERS FOR AROMATIZING PURPOSES

[75] Inventors: Johannes T. De Heij, Hilversum;
Franciscus P. Van Lier, Huizen;
Harrie Renes, Nederhorst den Berg,
all of Netherlands

[73] Assignee: Unilever Patent Holdings B.V.,
Vlaardingen, Netherlands

[21] Appl. No.: 970,870

[22] Filed: Nov. 3, 1992

[30] Foreign Application Priority Data

Nov. 4, 1991 [EP] European Pat. Off. ........ 91202864.4

[51] Int. Cl.$^5$ .................... C07C 43/115; C07C 43/15;
C07C 43/162; A61K 7/46
[52] U.S. Cl. .................................. 568/664; 568/668;
568/667; 512/22
[58] Field of Search ....................... 568/664, 668, 667;
512/22

[56] References Cited

U.S. PATENT DOCUMENTS 2,377,714  7/1942  Perkins ................................ 568/644
2,671,114  3/1954  Ipatieff et al. .
3,781,368  12/1973  Neale .................................... 568/664

FOREIGN PATENT DOCUMENTS 389945   3/1989  European Pat. Off. .
0413162  2/1991  European Pat. Off. .
489026  10/1936  United Kingdom .

OTHER PUBLICATIONS

Chem. Abstracts, vol. 40, p. 1460, (1946); Meunier et al.

Primary Examiner—Marianne M. Cintins
Assistant Examiner—Margaret J. Page
Attorney, Agent, or Firm—Cushman Darby & Cushman

[57] ABSTRACT

The invention relates to novel ethers and their use as aroma precursors. The ethers are derived from ionol and related compounds. These aroma precursors do not have a substantial aroma as such under ambient conditions, but will break up into a complex mixture having useful organoleptic properties under heating. The ethers are especially suitable for use in products which are heated, burned or smouldered in some stage of their use. The compounds according to the invention are especially suitable for application to tobacco. Mixtures obtained by degrading (e.g. by heating) the ethers according to the invention may be used in a flavouring or perfuming mixture as well due to their organoleptic properties.

8 Claims, No Drawings

ETHERS FOR AROMATIZING PURPOSES

The present invention relates to ethers and to their use as aroma precursors. More specifically the invention relates to ethers derived from ionol or related compounds and to their decomposition into aroma compounds on heating. Additionally, the invention relates to a process for preparing said ethers.

In the art of flavouring it is known to use so called precursor compounds which themselves do not have the desired organoleptic properties, but which under the conditions of use of the flavoured products decompose, thus giving a desired flavour compound. Simple esters such as acetates of flavouring alcohols have been used for this purpose.

However, there is a constant need for new aroma precursors which themselves are relatively non-volatile, which are reasonably thermostable and only break up into volatile aromatizing compounds on substantial heating or under pyrolysing conditions.

Also there is a need for aroma precursors which, on decomposition, provide a well-balanced mixture of aroma notes rather than merely a single aromatizing compound.

It has now been found that ethers derived from ionol or related compounds exhibit no substantial aroma as such, but on heating break up into complex aromatizing mixtures or compositions of volatile compounds.

The ethers according to the invention have the formula $R_1$—O—$R_2$, with $R_1$ and $R_2$ being radicals according to the following structural formula:

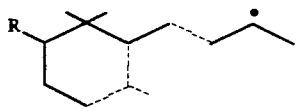

wherein R denotes either hydrogen or a lower alkyl group. Preferably R is hydrogen or methyl. Double bonds may be present at the positions indicated by the dotted lines. Preferably at least one double bond is present in the radicals $R_1$ and $R_2$. Furthermore, $R_1$ and $R_2$ can be either the same or different. More preferred are di-ionyl ethers i.e. ethers derived from $\alpha$, $\beta$ or $\gamma$-ionol.

The ethers according to the invention are not only novel as aroma precursors, but these compounds are also novel as such.

It is possible to use only one ether compound according to the above formula in an aromatizing composition, but if desired, mixtures of two or more of said ether compounds may be used in such a composition.

It was found that ether synthesis starting from ionol-type alcohols using a Lewis acid as a catalyst is a suitable method for synthesizing ethers according to the invention. Such a method has been described for the synthesis of other ethers by S. Kim et al. in J.Org.Chem. 52, 3917–3919 (1987). Kim et al. indicate that dichloro ethane may be used as a solvent in this reaction, but in the case of synthesizing the ethers according to the invention other common solvents, e.g. hydrocarbons such as hexane, gave good results as well. It was found that zinc halides, and in particular zinc chloride are suitable Lewis acid catalysts. The desired ethers can be isolated from the reaction mixture in a conventional way. "Aroma" is herein used as a collective term for perfume and flavour. In this connection, "aromatizing composition" is used as a collective term for perfume composition and flavouring composition, and similarly "aromatizing" is used as a collective term for flavouring and perfumery.

The compounds according to the invention can be added as such to a product to provide a flavour or odour on heating the said product or they can be incorporated first in a mixture which can be used as a flavour composition or perfume composition for application to such a product. In this connection the terms "flavouring composition" and "perfume composition" mean mixtures of flavouring components or perfume components respectively and/or other components, if desired dissolved in a suitable solvent or mixed with a powdered substrate or processed to form a powdered product. Such flavouring or perfume compositions may also include other flavouring or perfume precursor systems respectively. The said compositions are used to impart a desired flavour or odour to products of all types or to reinforce, to improve or to change the flavour or odour which these products already have or develop, or change the flavour or odour on usage of these products.

Alternatively, organoleptically useful mixtures, hereinafter referred to as "organoleptic mixtures", will be developed when the ethers according to the invention are thermally degraded as such. Said organoleptic mixtures may thereafter be used for flavouring or perfuming purposes, either by adding them as such to products to be flavoured or perfumed, or as a part of a flavouring or perfume composition.

Basic perfume and flavour substances which can be advantageously combined with the compounds according to the invention or the said organoleptic mixtures are, for example, natural products such as extracts, essential oils, absolutes, resinoids, resins, concretes etc., but also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such basic substances are mentioned, for example, in S. Arctander, Perfume and Flavor Chemicals (Montclair, N.J., 1969), in S. Arctander, Perfume and Flavor Materials of Natural Origin (Elizabeth, N.J., 1960), in T. E. Furia et al., CRC Fenaroli's Handbook of Flavor Ingredients, 2nd edition (Cleveland, CRC Press Inc., 1983), H.B. Heath, Source Book of Flavours, The Avi Publishing Co. Inc. Westport, Conn. (1981and "Flavor and Fragrance Materials—1991", Allured Publishing Co. Wheaton, Ill. USA.

Examples of perfume components which can be used in combination with the compounds according to the invention or with said organoleptic mixtures are geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butyl cyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)-propanal, 3-(p-tert-butylphenyl)propanal, tricyclodecenyl acetate, triclyclodecenyl propionate, 4-(4-hydroxy-4-methyl-pentyl)-3-cyclohexenecarbaldehyde, 4-(4-methyl-3-pentenyl)-3-cyclohexenecarbaldehyde, 4- acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, iomethylionones, irones, cis-3-hexenol and esters thereof, indan musks tetralin musks isochroman musks macrocyclic ketones, macrolactone musks ethylene brassylate, aromatic nitromusks.

Auxiliary materials and solvents which can be used in perfume compositions which contain compounds according to the invention are, for example: ethanol, isopropanol, diethyleneglycol monoethyl ether, diethyl phthalate etc. Such auxiliary materials and solvents for flavour compositions are, for example: ethanol, diethyleneglycol monoethyl ether, propylene glycol, glycerol and triacetin.

The quantities of the compounds according to the invention or said organoleptic mixtures to be used may be strongly divergent and depend, inter alia, on the product in which the compounds are used and on the nature and the quantity of the other components of a flavouring or perfume composition. In perfume and flavouring compositions an amount of 0.01% or more of the compounds according to the invention will generally have a clearly perceptible organoleptic effect. The amount of compounds according to the invention present in end products will generally be 0.01 ppm or more.

The products to which the ethers according to the invention can be added, either as such or in a composition or on a suitable carrier, are numerous. Application to products which are in some stage submitted to a heating, smouldering or burning step is especially suitable, because then an odour and/or flavour will be released on usage of said products. Products of this type include, inter alia, candles, ironing aids, matches, aids for lighting a fire, fuel for e.g. lighters, lamps and the like, products used with or intended for cooking, frying, baking, barbequeing or microwave heating. Other suitable applications may be products intended for cleaning purposes where heating is applied during some stage of the cleaning process, such as oven cleaners, detergents, fabric washing compositions, fabric softeners, flat-iron cleaners etcetera.

It is also possible to combine degraded and undegraded ethers according to the invention for flavouring and/or perfumery purposes.

As outlined above, the ethers according to the invention are easily degraded by heat, especially in the presence of oxygen or an oxygen containing gas such as air. Because the ethers according to the invention are yet relatively thermostable, it is preferred that the ethers according to the invention or products containing them are heated to at least 60° C. Under these conditions, complex mixtures having desirable organoleptic properties are developed. For the development of said complex mixtures it is more preferred that the ethers are heated to 120° C. or above, even more preferably to 150° C. or above.

The time needed for the development of a sufficiently strong odour or flavour will depend, inter alia, on the specific products whereto the ethers according to the invention are applied and the maximum temperature reached.

The compounds according to the invention and the said organoleptic mixtures are especially suitable for flavouring tobacco, tobacco products and tobacco substitutes or other materials used for the manufacturing of tobacco products such as e.g. cigarette wrappers. The term "tobacco" will be understood herein to mean natural products such as, for example, Virginia, Burley, Turkish or Maryland tobacco, flue-cured tobacco and others including tobacco-like or tobacco-based products such as reconstituted or homogenized leaf and the like. In this connection "tobacco products" mean tobacco or tobacco substitute containing products designed, intended or used for smoking, such as cigarettes, cigars, pipe tobacco etcetera. The term "tobacco substitutes" is to be understood herein to be compounds, compositions, materials or structures intended to replace natural tobacco or tobacco products partly or completely. The flavour is released to the smoke immediately or shortly after the tobacco products or tobacco substitutes are used as intended, i.e. smoked.

A number of ways are possible for applying the compounds according to the invention (either as such or as a part of a composition) to tobacco products or tobacco substitutes, strongly depending on the specific nature of the product or substitute.

In the case of tobacco, methods for applying flavours or flavouring compositions are known in the art and include simply spraying or atomizing the flavour or flavouring composition (sometimes diluted with a suitable solvent like alcohol) over the bulk of the tobacco. Another method may be finely dispersing an emulsion over the bulk of the tobacco, wherein the emulsion comprises an emulsifier, an aqueous phase, and an oil phase, which may comprise compound I, II, III or a combination thereof. Other compounds may be included in the formulation. Such a method is described in more detail in EP-A-366 835. Still another method for applying the flavour compounds to the tobacco is a method in which the flavour components (optionally mixed with other components) are micro-encapsulated and subsequently mixed with the tobacco bulk. Optionally an adhesive may be used to fix the micro-capsules to the tobacco leafs. Thus, tobacco, tobacco products or tobacco substitutes flavoured with the compounds according to the invention, either as such or as a part of a composition, can be obtained.

The invention is illustrated by the following examples but is in no way limited thereto.

EXAMPLE 1

Preparation of Di-$\beta$-Ionyl Ether

Zinc dichloride (1.4 kg) was added to hexane (45 kg) together with $\beta$-ionol (11 kg), all components being substantially dry, and the mixture was stirred at 20° C. for 2.5 hours. Hereafter the mixture was thoroughly washed (by stirring for 15 minutes and subsequent phase separation) with a mixture of 4.5 kg methanol and 0.5 kg water (twice), and 5 kg water. The solution was then dried with sodium sulphate, whereafter the hexane was boiled off under reduced pressure at 30° C., during which 40kg of hexane was recovered. 10.0 kg of $\beta$-dionyl ether was obtained.

EXAMPLE 2

A flavouring composition having a Virginia tobacco flavour was prepared by mixing the following compounds in the amounts indicated (in parts by weight on a total of 1000):

| | |
|---|---|
| Benzyl alcohol | 263 |
| γ-Butyrolactone | 250 |
| Ethyl palmitate | 200 |
| Acetic acid | 60 |
| γ-Valerolactone | 60 |
| Farnesol | 25 |
| Valeric acid | 20 |
| γ-Heptalactone | 20 |
| Ethyl laurate | 20 |
| Ethyl decanoate | 10 |
| Malt extract (20% dry matter) | 10 |
| Coffee extract | 10 |
| Furfural | 10 |
| Guajacol | 5 |
| Benzaldehyde | 4 |
| Acetophenone | 4 |
| Methylheptenone | 4 |
| Di-β-ionyl ether | 25 |

EXAMPLE 3

A composition suitable for flavouring the side stream smoke of tobacco, tobacco products or tobacco substitutes was prepared by mixing the following compounds in the amounts indicated (in parts by weight on a total of 1000):

| | |
|---|---|
| Apricot oleoresin | 350 |
| Olibanum resin | 30 |
| Vanilline | 25 |
| Sandalwood oil | 5 |
| Ylang Ylang oil | 2 |
| Coriander oil | 2 |
| Di-β-ionyl ether | 10 |
| Propylene glycol | 576 |

We claim:

1. An ether having the formula $R_1$—O—$R_2$ wherein $R_1$ and $R_2$ are radicals according to the following formula:

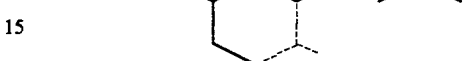

and wherein:

R denotes either hydrogen or a lower alkyl group, and double bonds can be present at the positions indicated by the dotted lines.

2. An ether according to claim 1, wherein R is hydrogen.

3. An ether according to claim 1, wherein R is methyl.

4. An ether according to any one of claims 1-3, wherein $R_1$ and $R_2$ are the same.

5. An ether according to any one of claims 1-3, wherein $R_1$ and $R_2$ are different.

6. An ether according to claim 1, wherein $R_1$ and $R_2$ are ionyl radicals.

7. An ether according to claim 1, wherein the ether decomposes to at least one volatile aromatizing compound when heated.

8. A composition intended to be at least partially heated, smouldered or burned, comprising at least one ether according to claim 1.

* * * * *